US012740820B2

(12) United States Patent
Phillips et al.

(10) Patent No.: US 12,740,820 B2
(45) Date of Patent: Sep. 22, 2026

(54) ADAPTING COMPONENT FOR ENABLING CRYOGENIC CARDIAC DEVICE USE IN NERVE BLOCK

(71) Applicant: AtriCure, Inc., Mason, OH (US)

(72) Inventors: George Phillips, Norwood, OH (US); Craig Crandall, Rising Sun, IN (US)

(73) Assignee: AtriCure, Inc., Mason, OH (US)

( * ) Notice: Subject to any disclaimer, the term of this patent is extended or adjusted under 35 U.S.C. 154(b) by 253 days.

(21) Appl. No.: 18/674,504

(22) Filed: May 24, 2024

(65) Prior Publication Data

US 2025/0359915 A1 Nov. 27, 2025

(51) Int. Cl.

| | |
|---|---|
| ***A61B 18/02*** | (2006.01) |
| ***A61B 17/00*** | (2006.01) |
| ***A61B 18/00*** | (2006.01) |
| ***A61M 25/00*** | (2006.01) |

(52) U.S. Cl.

CPC .... *A61B 18/02* (2013.01); *A61B 2017/00336* (2013.01); *A61B 2017/00486* (2013.01); *A61B 2018/00351* (2013.01); *A61B 2018/00434* (2013.01); *A61B 2018/00577* (2013.01); *A61B 2018/0091* (2013.01); *A61B 2018/0212* (2013.01); *A61M 2025/0004* (2013.01)

(58) Field of Classification Search

CPC .......... A61B 18/02; A61B 2017/00336; A61B 2017/00486

See application file for complete search history.

(56) References Cited

U.S. PATENT DOCUMENTS

| | | | | |
|---|---|---|---|---|
| 9,408,529 B2 * | 8/2016 | Smith | .................. | A61B 1/0055 |
| 2010/0280316 A1 * | 11/2010 | Dietz | .................. | A61B 8/4466 600/101 |

FOREIGN PATENT DOCUMENTS

| | | | | |
|---|---|---|---|---|
| CN | 103096826 B * | 7/2016 | ........... | A61B 18/082 |

* cited by examiner

*Primary Examiner* — Linda C Dvorak
*Assistant Examiner* — William Mossbrook
(74) *Attorney, Agent, or Firm* — Levine Bagade Han LLP

(57) ABSTRACT

Disclosed herein are systems and methods for performing a cardiac arrhythmia and a subsequent nerve block. A cryogenic device can be provided and can comprise a handle comprising a proximal end and a distal end, an elongate shaft extending from the handle, the elongate shaft comprising a lumen, a cryogenic probe extending from the elongate shaft, wherein the cryogenic probe is flexible, and an adapter removably located at a distal end of the elongate shaft, the adapter comprising a base portion, a head portion, and an opening therethrough, wherein the base portion comprises one or more prongs configured to key onto the elongate shaft, wherein the head portion is rounded and comprises a groove embedded within. The adapter can be configured to receive the cryogenic probe via the opening and within the groove such that the cryogenic probe maintains a shape when coupled to the groove.

14 Claims, 4 Drawing Sheets

ADAPTING COMPONENT FOR ENABLING CRYOGENIC CARDIAC DEVICE USE IN NERVE BLOCK

FIELD OF TECHNOLOGY

The present disclosure relates generally to the field of cryogenic devices, and more specifically, treating cardiac arrhythmias and performing nerve blocks.

BACKGROUND

Current devices used for treatment of cardiac arrhythmia and nerve blocks often comprise similar features. Such devices that are planned for nerve block can have end effectors in small sizes (i.e., 8 mm to 10 mm diameter). Since, for nerve blocks, the parts of the intercostal space can exceed 10 mm as nerves tend to branch more as they move further from the spinal cord, the user may need to perform multiple freezes. This increases the total duration of the procedures.

Further, probes for the treatment of cardiac arrhythmia devices are often flexible to bend in any shape needed to cover the surface of the heart. However, the flexibility of the probe can be such that the probe does not maintain its shape within intercostal spaces. The probe can thus be difficult to manage for a nerve block. Devices for treatment of cardiac arrythmias are long (~10 cm) and slender (~4 mm in diameter) probes meant to be bent in different shapes.

Therefore, there remains a need for methods and devices for devices and methods that allow a user to both treat a cardiac arrhythmia and perform a nerve block with minimal devices, lowering procedure times and costs.

SUMMARY

Disclosed herein are systems and methods for performing a treatment of cardiac arrhythmia and a subsequent nerve block. A cryogenic device can be provided and can comprise a handle comprising a proximal end and a distal end, an elongate shaft extending from the handle, the elongate shaft comprising a lumen, a cryogenic probe extending from the elongate shaft, wherein the cryogenic probe is flexible, and an adapter removably located at a distal end of the elongate shaft, the adapter comprising a base portion, a head portion, and an opening therethrough, wherein the base portion comprises one or more prongs configured to key onto the elongate shaft, wherein the head portion is rounded and comprises a groove embedded within. The adapter can be configured to receive the cryogenic probe via the opening and within the groove such that the cryogenic probe maintains a shape when coupled to the groove.

The lumen of the elongate shaft can comprise a clover leaf groove within that couples to the one or more prongs. The cryogenic probe can be flexible and configured to bend towards the proximal end of the handle. The cryogenic probe can wrap around the adapter during bending towards the proximal end of the handle. The one or more prongs can deflect towards the cryogenic probe to stabilize the cryogenic probe. The base portion of the adapter can comprise a sleeve located concentrically around the elongate shaft. The cryogenic probe can comprise a cavity in fluid communication with one or more orifices. An exterior of the distal tip can comprise a thermal application surface.

A method according to one aspect of the invention can comprise performing a cardiac ablation at a target site with a cryogenic device. The cryogenic device can comprise a handle comprising a proximal end and a distal end, an elongate shaft extending from the handle, the elongate shaft comprising a lumen, a cryogenic probe extending from the elongate shaft, wherein the cryogenic probe is flexible. The method can further comprise withdrawing the cryogenic device from the target site.

The method can further comprise attaching an adapter at a distal end of the elongate shaft. The adapter can comprise a base portion, a head portion, and an opening therethrough, wherein the base portion comprises one or more prongs configured to key onto the elongate shaft, wherein the head portion is rounded and comprises a groove embedded within. The method can further comprise bending the cryogenic probe along the groove of the adapter such that the cryogenic probe maintains a shape when coupled to the groove. The method can further comprise performing an intercostal nerve block with the cryogenic device.

DETAILED DESCRIPTION

The exemplary embodiments of the present disclosure are described and illustrated below to encompass exemplary cryogenic devices and, more specifically, encompass cryogenic devices and methods of manufacturing the same, where the cryogenic devices can be used for surgical applications to deliver cooling to one or more tissue locations. In addition, the exemplary embodiments are directed to methods of using cryogenic devices as part of surgical procedures. Of course, it will be apparent to those of ordinary skill in the art that the embodiments discussed below are exemplary in nature and can be reconfigured without departing from the scope and spirit of the present invention. However, for clarity and precision, the exemplary embodiments as discussed below can include optional steps, methods, and features that one of ordinary skill should recognize as not being a requisite to fall within the scope of the present invention.

Figure 1A:
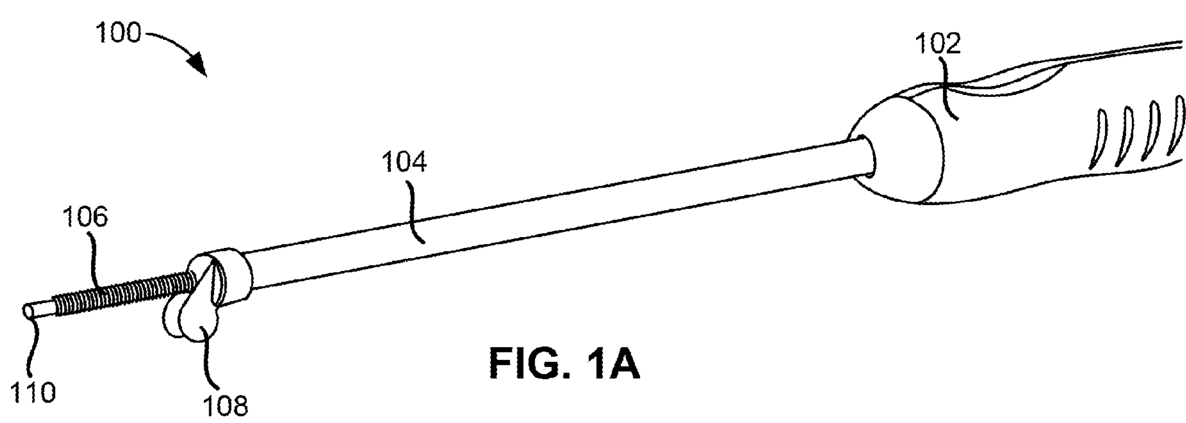
FIG. 1A illustrates a perspective view of a cryogenic device in accordance with one variation of the present invention.

FIG. 1A illustrates a perspective view of a cryogenic device 100 in accordance with one variation of the present invention. The cryogenic device 100 comprises a handle 102, an elongate shaft 104, a cryogenic probe 106, and an adapter 108. The elongate shaft can comprise a lumen within through which the cryogenic probe 106 can be disposed within. The cryogenic probe 106 can comprise a distal tip 110 at a distal end of the probe 106. The adapter 108 can be disposed at a distal end of the elongate shaft 104 and can be disposed about the cryogenic probe 106.

The elongate shaft 104 has a smooth outer surface over its entire length and can be made of polycarbonate. The shaft 104 can extend from and can be secured to the handle 102.

In this exemplary embodiment, the cryogenic device 100 has an overall length of approximately 43 cm, with the cryogenic probe 106 having a variable length of up to approximately 10 cm, and the elongate shaft 104 and the handle 102 having a combined length of approximately 33 cm. If employed in a robotic device, the length of the probe tube may vary. All materials used in the cryogenic device 100 that are exposed to the cryofluid may be compatible with the cryofluid used in the device, and components intended for patient contact may be biocompatible. The device (and its packaging) may also be gamma stable, as gamma sterilization is an exemplary sterilization method.

The cryogenic probe 106 can be constructed of a relatively soft metal, such as Series 1000 aluminum alloy. Alternatively, gold, gold alloys, stainless steel, nitinol, or other malleable metallic alloys that have suitable thermal conductivity may be used. In exemplary form, the cryogenic probe 106 is malleable and formed into various shapes appropriate for making the different ablation lines, but is stiff enough for tissue conformance and to maintain its shape when applied to cardiac tissue without any secondary reinforcement. Likewise, the exemplary end effector is capable of being bent in an arcuate manner to have a minimum radius of approximately 0.5 in.

Inside the cryogenic probe 106 a Joule-Thomson Effect is formed where the cryofluid undergoes expansion. The Joule-Thomson Effect is created by the expansion of gas that occurs as the cryofluid moves through the small orifice from each of the high-pressure supply tubes into the low pressure expansion chamber comprised by the probe tube. Temperatures within the probe tube can fall below −60° C., and provide for surface temperatures of the end effector to reach less than −45° C., when nitrous oxide gas is used as the cryofluid.

The cryogenic probe 106 can house a plurality of separate gas delivery passageways in the form of malleable supply tubes or hypotubes. Each of the supply tubes can terminate in a reduced orifice that forms a nozzle to deliver the gas into the expansion chamber. Each nozzle has a cross-sectional area that achieves a flow rate of 600-630 ccm at 15 psi. In practice, this results in the individual orifices having an inside diameter of from about 0.003 to about 0.010 in. and a corresponding cross-sectional area of from about 0.00000707 sq. in. to about 0.0000785 sq. in. The orifices are staggered lengthwise at 0.7 to 0.9 in. (2 cm) intervals.

The three cryofluid supply tubes can be connected at their proximal ends to a single cryofluid delivery tube. The three cryofluid supply tubes can terminate in the fluid expansion chamber (i.e., within the probe 106), the internal diameter of which may be of sufficient cross-sectional area to allow managed evacuation of the expanding cryofluids. The flow of the cryofluid through the probe tube and into the remaining exhaust tubing system may be controlled.

In exemplary form, the cryoprobe may be configured to allow relative axial movement between the cryogenic probe 106 and the elongated shaft 104 and handle 17, such that the cryogenic probe 106 may be retracted into the elongated shaft 104 to protect it when not in use.

The cryogenic probe 106 can include different sections that exhibit different flexibilities. As used herein, "flexible" or "flexibilities" can describe a property of a component that is elastically and/or plastically deformable when subject to forces consistent with normal, intended use.

Figure 1B:
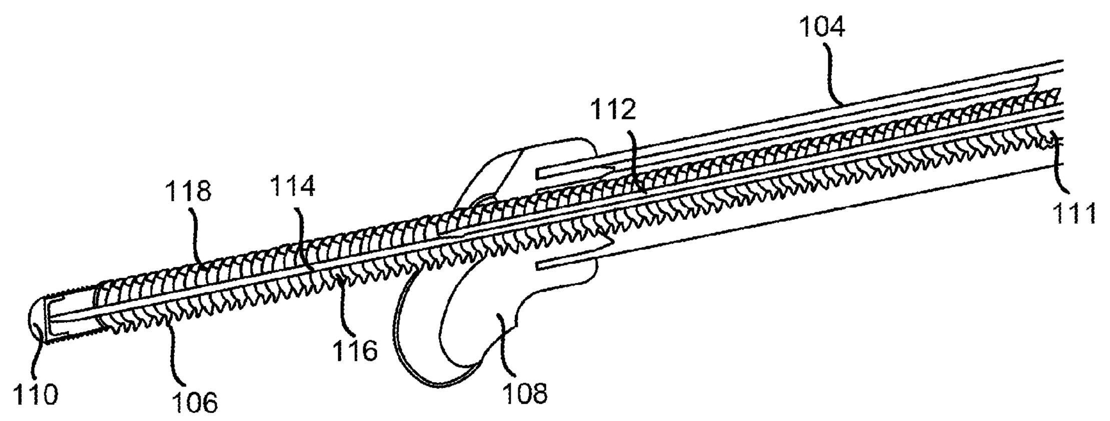
FIG. 1B illustrates a close-up view of a distal end of the cryogenic device of FIG. 1A.

FIG. 1B illustrates a close-up view of a distal end of the cryogenic device of FIG. 1A. The cryogenic probe 106, which can be made of stainless steel, can comprise one or more conduits disposed within. Alternatively, the cryogenic probe 106 can be made of aluminum, copper, or other types of metal. The one or more conduits can comprise one or more supply conduits 112, 114 that supply cryogenic fluid to the probe 106 and an exhaust conduit 116 between the nozzles 112, 114 and the inner wall of the probe 106 that discharges spent cryogenic fluid within the probe 106 (e.g., within a cavity of the probe). The supply conduits 112, 114 can supply cryogenic fluid (e.g., nitrous oxide ($N_2O$), carbon dioxide ($CO_2$)) to the probe 106 under conditions to cool an active region of the probe 106 that is operative to ablate tissue coming into contact with the exterior and active region while the cryogenic fluid flows through the device 100, which in exemplary form allows an operator to create lines of ablation through tissue, such as cardiac tissue. In other variations, there may be three or more inlet nozzles within the probe 106.

The cryogenic probe 106 can be constructed of a relatively soft metal, such as Series 1000 aluminum alloy. Alternatively, gold, gold alloys, stainless steel, nitinol, or other malleable metallic alloys that have suitable thermal conductivity may be used. In exemplary form, the cryogenic probe 106 is malleable and formed into various shapes appropriate for making the different ablation lines, but is stiff enough for tissue conformance and to maintain its shape when applied to cardiac tissue without any secondary reinforcement. Likewise, the exemplary end effector is capable of being bent in an arcuate manner to have a minimum radius of approximately 0.5 in. A spring 118 can be positioned within the probe 106 to flex the probe as desired as well as adding rigidity to the probe 106. The outer surface of the probe 106 can be smooth such that the entire outer surface of the probe can contact tissue uniformly and along the entire length of the probe 106. FIGS. 2A to 2D illustrate various views of an adapter for use with the cryogenic device of the present invention. The adapter 108 can comprise a base portion 200, a head portion 202, and a curved transition portion 204 therebetween. The adapter 108 can be attached to the elongate shaft 104 before certain procedures to be used with the adapter 108.

The base portion 200 can comprise a cylindrical shape comprising one or more prongs or splines 206 extending from a bottom of the base portion 200. The one or more splines 206 can be configured to key or lock within the lumen 111 of the elongate shaft 104 such that the one or more splines 206 extend from the distal end of the elongate shaft 104.

Figure 1C:
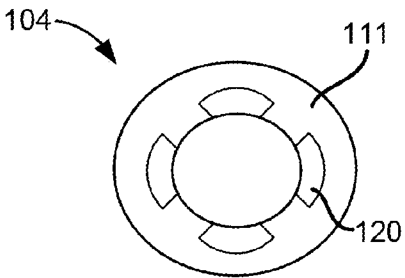
FIG. 1C illustrates a cross-sectional view of an elongated shaft of the cryogenic device.
Figure 2A:
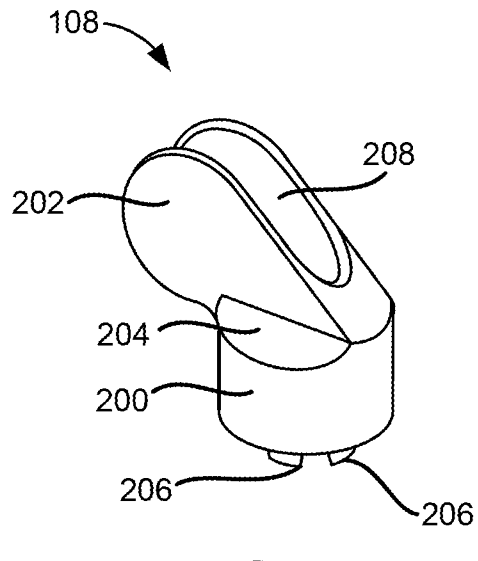
FIGS. 2A to 2D illustrate various views of an adapter for use with the cryogenic device of the present invention.
Figure 2B:
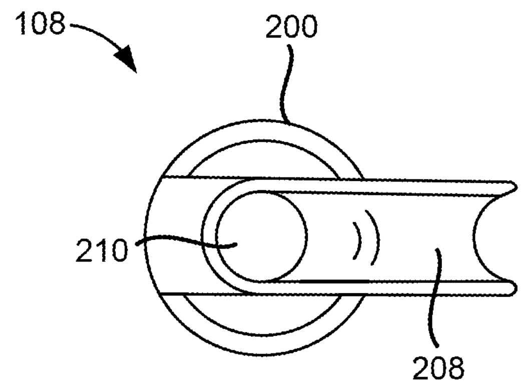
Figure 2C:
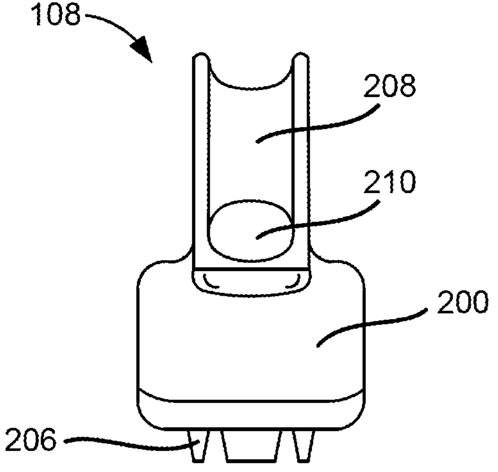
Figure 2D:
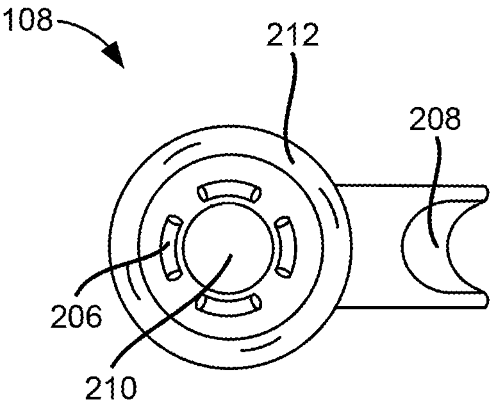

As seen in FIG. 1C, the lumen 111 can comprise a clover leaf groove 120 within that couples to the one or more splines such that the adapter 108 withstands rotation when coupled with the elongate shaft 104. The base portion 200 can comprise a sleeve 212 that is positioned around concentrically the elongate shaft 104 when the adapter 108 is coupled to the elongate shaft 104 to provide support for and stabilize the adapter 108. The one or more splines 206 can deflect towards the cryogenic probe 106 to stabilize the cryogenic probe 106.

The head portion 202 can be rounded or slanted and can comprise a groove 208 embedded within and at an angle with respect to a longitudinal axis of the adapter 108. The groove 208 can be formed within the head portion 202 such that the groove 208 creates a circular shape at the head portion 202.

The adapter 108 can comprise an opening 210 therethrough along the longitudinal axis of the adapter. The opening 210 be configured and sized to receive the cryogenic probe 106. The cryogenic probe 106 can be fed through the opening 210 and wrapped along the groove 208 such that the distal tip 110 of the probe 106 faces a proximal end of the handle 102 of the device 100.

The adapter 108 can be made of polycarbonate, polyethylene, PMMA, and PETG. The adapter can be biocompatible and insulative for use within the anatomy. The head portion 202 can comprise a total length of about 8 mm to about 20 mm.

Figures 3A, 3B, 3C:
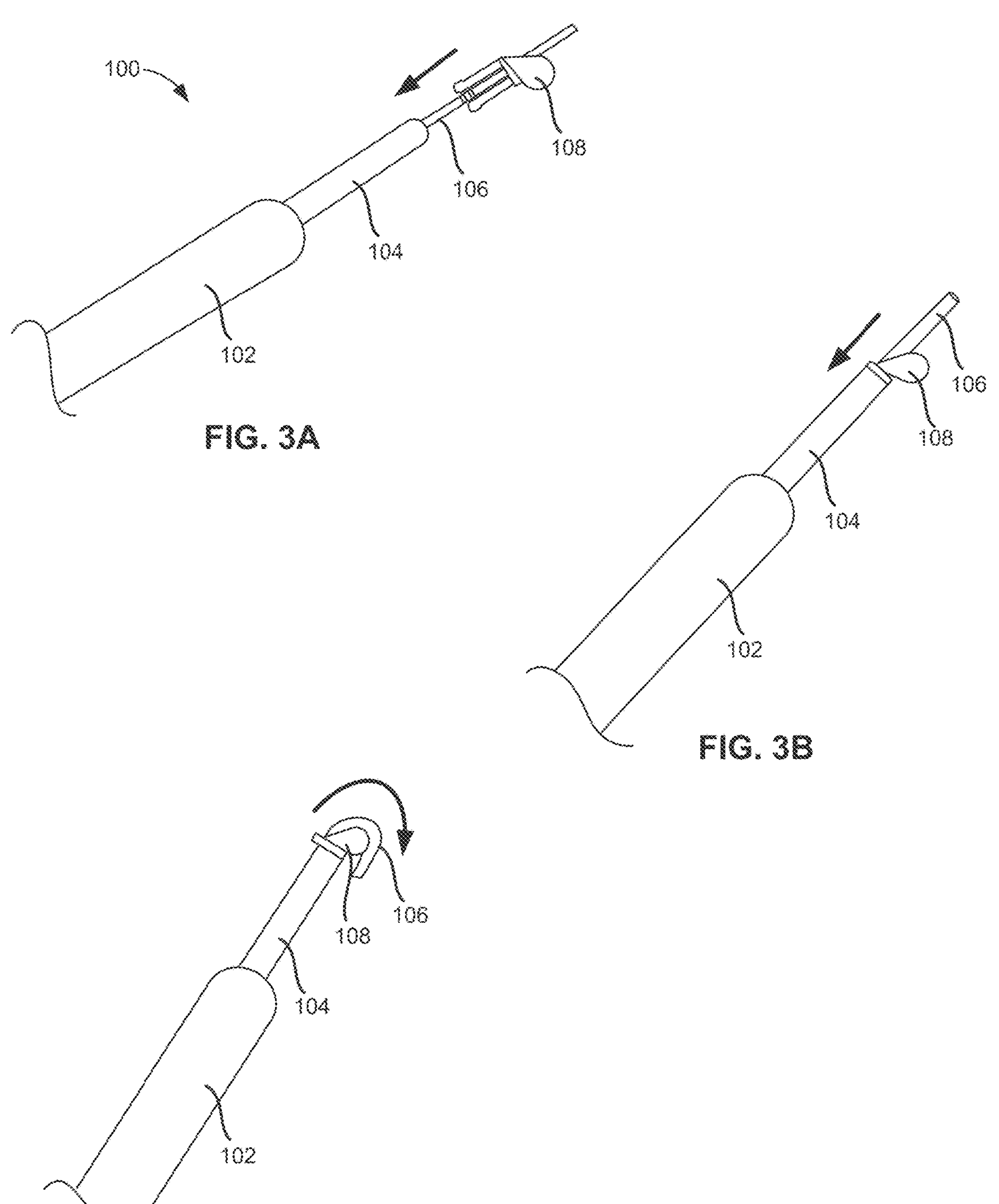
FIGS. 3A to 3C illustrate perspective views of the adapter being used with a cryogenic probe in accordance with one variation of the present invention.

FIGS. 3A to 3C illustrate perspective views of the adapter being used with a cryogenic probe 106 in accordance with one variation of the present invention. The adapter 108 can be coupled to the elongate shaft 104 after the cryogenic probe 106 is advanced through the lumen 111 of the elongate shaft 104, as seen in FIG. 3A. Alternatively, the adapter 108 can be placed on the elongate shaft 104 before the cryogenic probe 106 is advanced through the lumen 111 of the elongate shaft 104.

Once the adapter 108 is placed on the elongate shaft 104, the user can bend the probe 106 to wrap around the adapter 108, as seen in FIG. 3C. The probe 106 can comprise variations of bend features (i.e., different sizes) which the user can choose from depending on the specific patient anatomy. The probe 106 can comprise a bend radius of about 0 degrees to about 270 degrees around the adapter 108. The adapter 108 can also be used with a variety of existing cryogenic devices.

Cryogenic devices are often used for treating cardiac arrhythmias and/or forming nerve blocks. The addition of the adapter 108 allows a user to perform a nerve block with the same cryogenic device as used for cardiac arrhythmia. Creating lesions in the treatment of cardiac arrhythmias often require the probe 106 to be flexible enough to bend to cover a large surface of the heart. To perform a nerve block, however, the device needs to be introduced through an intercostal space. After the cardiac arrhythmia treatment, the device can be withdrawn and the adapter 108 can be attached thereon. To maintain the shape of the flexible probe 106 during this introduction and within the intercostal space, the adapter 108 can be used to strengthen the probe. This allows the user to use a single cryogenic device to perform both treatment of a cardiac arrhythmia and nerve block, saving time.

Figure 4:
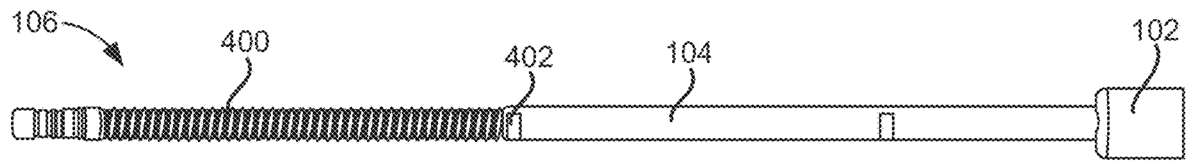
FIG. 4 illustrates a side view of a cryogenic device in accordance with another variation of the present invention.

FIG. 4 illustrates a side view of a variation of the cryogenic device 100. The device 100 can comprise a thermocouple 400 that is wrapped around the probe 106 and configured to measure temperature at the target site. An adhesive 402 can be applied between the thermocouple 400 and the elongate shaft 104 to hold the thermocouple 400 in place. The thermocouple 400 can be configured to flex and bend with the probe 106.

In addition, the device may be provided with a system for determining the surface temperature of the end effector and providing the user with that data. To this end, the outer surface of the probe tube may be provided with the thermocouple 400. The thermocouple 400 can be located on the cryogenic probe 106. Wiring on the outside of the cryogenic probe 106 transmits signals generated by the thermocouple to a display (not shown) having a read-out visible to the user. The thermocouple 400 may be a type T calibration thermocouple which can range between −250° C. and 350° C.

A number of embodiments have been described. Nevertheless, it will be understood by one of ordinary skill in the art that various changes and modifications can be made to this disclosure without departing from the spirit and scope of the embodiments. Elements of systems, devices, apparatus, and methods shown with any embodiment are exemplary for the specific embodiment and can be used in combination or otherwise on other embodiments within this disclosure. For example, the steps of any methods depicted in the figures or described in this disclosure do not require the particular order or sequential order shown or described to achieve the desired results. In addition, other steps or operations can be provided, or steps or operations can be eliminated or omitted from the described methods or processes to achieve the desired results. Moreover, any components or parts of any apparatus or systems described in this disclosure or depicted in the figures can be removed, eliminated, or omitted to achieve the desired results. In addition, certain components or parts of the systems, devices, or apparatus shown or described herein have been omitted for the sake of succinctness and clarity.

Accordingly, other embodiments are within the scope of the following claims and the specification and/or drawings can be regarded in an illustrative rather than a restrictive sense.

Each of the individual variations or embodiments described and illustrated herein has discrete components and features which can be readily separated from or combined with the features of any of the other variations or embodiments. Modifications can be made to adapt a particular situation, material, composition of matter, process, process act(s) or step(s) to the objective(s), spirit, or scope of the present invention.

Methods recited herein can be carried out in any order of the recited events that is logically possible, as well as the recited order of events. Moreover, additional steps or operations can be provided or steps or operations can be eliminated to achieve the desired result.

Furthermore, where a range of values is provided, every intervening value between the upper and lower limit of that range and any other stated or intervening value in that stated range is encompassed within the invention. Also, any optional feature of the inventive variations described can be set forth and claimed independently, or in combination with any one or more of the features described herein. For example, a description of a range from 1 to 5 should be considered to have disclosed subranges such as from 1 to 3, from 1 to 4, from 2 to 4, from 2 to 5, from 3 to 5, etc. as well as individual numbers within that range, for example 1.5, 2.5, etc. and any whole or partial increments therebetween.

All existing subject matter mentioned herein (e.g., publications, patents, patent applications) is incorporated by reference herein in its entirety except insofar as the subject matter can conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

Reference to the phrase "at least one of", when such phrase modifies a plurality of items or components (or an enumerated list of items or components) means any combination of one or more of those items or components. For example, the phrase "at least one of A, B, and C" means: (i) A; (ii) B; (iii) C; (iv) A, B, and C; (v) A and B; (vi) B and C; or (vii) A and C.

In understanding the scope of the present disclosure, the term "comprising" and its derivatives, as used herein, are intended to be open-ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" "element," or "component" when used in the singular can have the dual meaning of a single part or a plurality of parts. As used herein, the following directional terms "forward, rearward, above, downward, vertical, horizontal, below, transverse, laterally, and vertically" as well as any other similar directional terms refer to those positions of a device or piece of equipment or those directions of the device or piece of equipment being translated or moved.

Finally, terms of degree such as "substantially", "about" and "approximately" as used herein mean the specified value or the specified value and a reasonable amount of deviation from the specified value (e.g., a deviation of up to ±0.1%, ±1%, ±5%, or ±10%, as such variations are appropriate) such that the end result is not significantly or materially changed. For example, "about 1.0 cm" can be interpreted to mean "1.0 cm" or between "0.9 cm and 1.1 cm." When terms of degree such as "about" or "approximately" are used to refer to numbers or values that are part of a range, the term can be used to modify both the minimum and maximum numbers or values.

It will be understood by one of ordinary skill in the art that the various methods disclosed herein can be embodied in a non-transitory readable medium, machine-readable medium, and/or a machine accessible medium comprising instructions compatible, readable, and/or executable by a processor or server processor of a machine, device, or computing device. The structures and modules in the figures can be shown as distinct and communicating with only a few specific structures and not others. The structures can be merged with each other, can perform overlapping functions, and can communicate with other structures not shown to be connected in the figures. Accordingly, the specification and/or drawings can be regarded in an illustrative rather than a restrictive sense.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that can become obvious to those skilled in the art in view of this disclosure.

We claim:

1. A cryogenic device, comprising:
- a handle comprising a proximal end and a distal end;
- an elongate shaft extending from the handle, the elongate shaft comprising a lumen;
- a cryogenic probe extending from the elongate shaft, wherein the cryogenic probe is flexible;
- an adapter removably located at a distal end of the elongate shaft, the adapter comprising a base portion, a head portion, and an opening therethrough, wherein the base portion comprises one or more prongs configured to key onto the elongate shaft, wherein the head portion is rounded and comprises a groove embedded within;
- wherein the adapter is configured to receive the cryogenic probe via the opening and within the groove such that the cryogenic probe maintains a shape when coupled to the groove.

2. The cryogenic device of claim 1, wherein the lumen of the elongate shaft comprises a clover leaf groove within that couples to the one or more prongs.

3. The cryogenic device of claim 1, wherein the cryogenic probe is flexible and is configured to bend towards the proximal end of the handle.

4. The cryogenic device of claim 1, wherein the cryogenic probe wraps around the adapter during bending towards the proximal end of the handle.

5. The cryogenic device of claim 1, wherein the one or more prongs deflect towards the cryogenic probe to stabilize the cryogenic probe.

6. The cryogenic device of claim 1, wherein the base portion of the adapter comprises a sleeve located concentrically around the elongate shaft.

7. The cryogenic device of claim 1, wherein the cryogenic probe comprises a cavity in fluid communication with one or more orifices, wherein an exterior of the cryogenic probe comprises a thermal application surface.

8. A method, comprising:
- performing a cardiac ablation at a target site with a cryogenic device, wherein the cryogenic device comprises:
  - a handle comprising a proximal end and a distal end;
  - an elongate shaft extending from the handle, the elongate shaft comprising a lumen;
  - a cryogenic probe extending from the elongate shaft, wherein the cryogenic probe is flexible;
- withdrawing the cryogenic device from the target site;
- attaching an adapter at a distal end of the elongate shaft, the adapter comprising a base portion, a head portion, and an opening therethrough, wherein the base portion comprises one or more prongs configured to key onto the elongate shaft, wherein the head portion is rounded and comprises a groove embedded within;
- bending the cryogenic probe along the groove of the adapter such that the cryogenic probe maintains a shape when coupled to the groove; and
- performing an intercostal nerve block with the cryogenic device.

9. The method of claim 8, wherein the lumen of the elongate shaft comprises a clover leaf groove within that couples to the one or more prongs.

10. The method of claim 8, wherein the cryogenic probe is flexible and is configured to bend towards the proximal end of the handle.

11. The method of claim 8, wherein the cryogenic probe wraps around the adapter during bending towards the proximal end of the handle.

12. The method of claim 8, wherein the one or more prongs deflect towards the cryogenic probe to stabilize the cryogenic probe.

13. The method of claim 8, wherein the base portion of the adapter comprises a sleeve located concentrically around the elongate shaft.

14. The method of claim 8, wherein the cryogenic probe comprises a cavity in fluid communication with one or more orifices, wherein an exterior of the cryogenic probe comprises a thermal application surface.

* * * * *